United States Patent
Rao et al.

(10) Patent No.: US 11,203,742 B2
(45) Date of Patent: Dec. 21, 2021

(54) SUCROSE PHOSPHORYLASE MUTANT WITH IMPROVED ENZYME ACTIVITY AND CONSTRUCTION METHOD THEREOF AND USE THEREOF

(71) Applicant: Jiangnan University, Wuxi (CN)

(72) Inventors: Zhiming Rao, Wuxi (CN); Peifeng Duan, Wuxi (CN); Jianing Zhang, Wuxi (CN); Xian Zhang, Wuxi (CN); Taowei Yang, Wuxi (CN); Meijuan Xu, Wuxi (CN); Minglong Shao, Wuxi (CN); Yu Liu, Wuxi (CN); Ziwei Wang, Wuxi (CN); Yan Chen, Wuxi (CN); Qi Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 16/895,658

(22) Filed: Jun. 8, 2020

(65) Prior Publication Data

US 2021/0130797 A1    May 6, 2021

(30) Foreign Application Priority Data

Oct. 31, 2019 (CN) .......................... 201911056382.9

(51) Int. Cl.
| | |
|---|---|
| C12N 9/10 | (2006.01) |
| C12N 1/21 | (2006.01) |
| C12N 15/54 | (2006.01) |
| C12N 1/20 | (2006.01) |
| C12N 15/63 | (2006.01) |

(52) U.S. Cl.
CPC ............ *C12N 9/1051* (2013.01); *C12N 1/20* (2013.01); *C12N 15/63* (2013.01); *C12Y 204/01007* (2013.01)

(58) Field of Classification Search
None
See application file for complete search history.

(56) References Cited

FOREIGN PATENT DOCUMENTS

CN    107858335 A    *    3/2018

OTHER PUBLICATIONS

Uniprot, Accession No. A0A223XR29, 2018, www.uniprot.org. (Year: 2018).*
Mueller et al., Dissecting differential binding of fructose and phosphate as leaving group/nucleophile of glucosyl transfer catalyzed by sucrose phosphorylase, FEBS Lett. 581, 2007, 3814-18. (Year: 2007).*
Goedl et al., Sucrose phosphorylase: a powerful transglucosylation catalyst for synthesis of a-D-glucosides as industrial fine chemicals, Biocatalysis Biotransformation 28, 2010, 10-21. (Year: 2010).*
Verhaeghe et al., Improving the glycosylation potential of sucrose phosphorylase through enzyme engineering, Dissertation, Ghent University, 2014. (Year: 2014).*

* cited by examiner

Primary Examiner — Robert B Mondesi
Assistant Examiner — Todd M Epstein
(74) Attorney, Agent, or Firm — Mintz Levin Cohn Ferris Glovsky and Popeo, P.C.

(57) ABSTRACT

The disclosure relates to a sucrose phosphorylase mutant with improved enzyme activity, and construction method thereof and use thereof, and belongs to the technical field of genetic engineering. The amino acid sequence of the mutant of the disclosure is as shown in SEQ ID NO: 1. The mutant of the disclosure is based on sucrose phosphorylase derived from *Leuconostoc mesenteroides*, and subjected to site-directed mutagenesis to improve the enzyme activity of sucrose phosphorylase. The mutant is expressed in *Corynebacterium glutamicum* and used as a whole cell catalyst to produce 2-O-α-D-glycerol glucoside. At a 5 L fermentation tank level, a large quantity of 2-O-α-D-glycerol glucoside can be produced efficiently in a short time, which is conducive to expanding the prospect of industrial application of sucrose phosphorylase for the production of 2-O-α-D-glycerol glucoside and realizing its large-scale industrial application.

15 Claims, 1 Drawing Sheet

Specification includes a Sequence Listing.

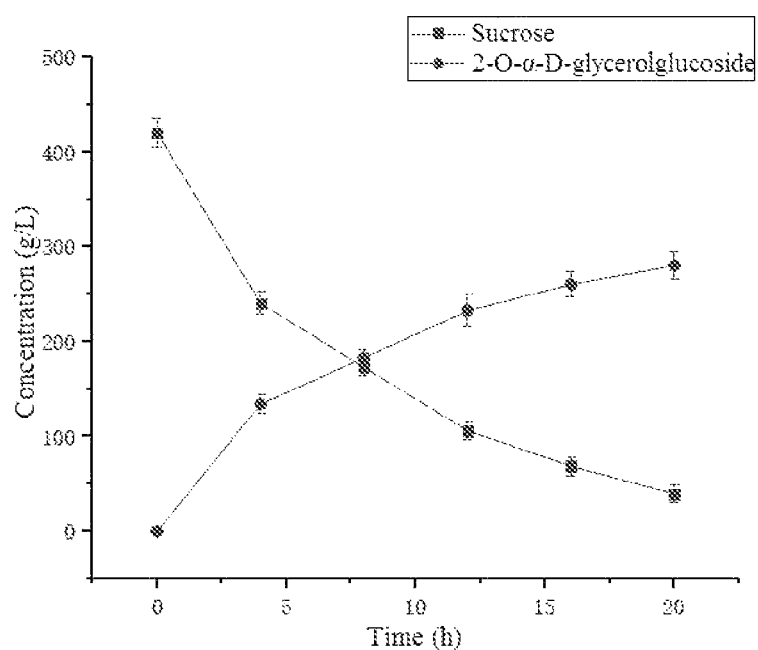

SUCROSE PHOSPHORYLASE MUTANT WITH IMPROVED ENZYME ACTIVITY AND CONSTRUCTION METHOD THEREOF AND USE THEREOF

SUBMISSION OF SEQUENCE LISTING ON ASCII TEXT FILE

The present application contains a sequence listing which has been submitted in ASCII format via EFS-Web and is hereby incorporated by reference in its entirety. The ASCII copy was created on Jun. 8, 2020, named 055767_511001US_SEQUENCE_LISTING.txt and is 13 KB in size. The aforementioned sequence listing forms part of the disclosure of the present application and is incorporated herein by reference in its entirety.

CROSS-REFERENCE TO RELATED APPLICATIONS

The present application claims priority to Chinese Patent Appl. No. 201911056382.9 to Rao et al., filed Oct. 31, 2019 and entitled "Sucrose Phosphorylase Mutant with Improved Enzyme Activity and Construction Method Thereof and Use Thereof", and incorporates its disclosure herein by reference in its entirety.

TECHNICAL FIELD

The invention relates to the technical field of genetic engineering, in particular to a sucrose phosphorylase mutant with improved enzyme activity, and construction method thereof and use thereof.

BACKGROUND

Sucrose phosphorylase (EC2.4.1.7, Sucurose Phosphorylase, Spase) is a specific enzyme that catalyzes the transfer of glucosidic bonds. It mainly catalyzes two types of reactions: one is the reaction that transfers the glucosyl group in glucose-1-phosphate to a receptor, e.g., if D-fructose is used as a receptor, it can produce sucrose under the catalysis of the enzyme; the other is the reaction that transfers the glucosyl group in sucrose to a receptor, and the receptor includes an inorganic phosphoric acid, water and substances containing phenolic hydroxyl groups, alcoholic hydroxyl groups and carboxyl groups; if phosphoric acid is used as the receptor, it can produce glucose-1-phosphate and D-fructose.

According to this catalytic property, the sucrose phosphorylase can use fructose, xylose, galactose, and rhamnose as receptors to catalyze the synthesis of corresponding oligosaccharides with an additional glucosyl group, such as 2-α-D-glucosyl-D-fructose, 1-α-D-glucosyl-D-xylose, 2-α-D-glucosyl-L-galactose, 2-α-D-glucosyl-rhamnose, etc.; and compounds containing alcoholic hydroxyl groups, phenolic hydroxyl groups and carboxyl groups can be modified and changed, e.g., the sucrose phosphorylase, can use glycerol as a receptor to catalyze the synthesis of 2-O-α-D-glycerol glucoside from sucrose, which is of great industrial value.

The enzyme activity of sucrose phosphorylase is relatively low, which limits the application of sucrose phosphorylase to the production of 2-O-α-D-glycerol glucoside in industry.

SUMMARY

The object of this disclosure is to provide a sucrose phosphorylase mutant with improved enzymatic activity, and construction method thereof and use thereof. The mutant has high enzyme activity, high substrate conversion rate, and high industrial application potential.

The disclosure provides a sucrose phosphorylase mutant with improved enzyme activity, and the amino acid sequence of the mutant is as shown in SEQ ID NO: 1.

The invention also provides a gene encoding the mutant according to the above technical solution, and the nucleotide sequence of the gene is as shown in SEQ ID NO: 3.

The disclosure also provides a recombinant expression vector containing the gene described in the above technical solution.

The disclosure also provides a genetic engineering strain expressing the sucrose phosphorylase mutant according to the above technical solution.

Preferably, the host strain of the genetic engineering strain includes *Corynebacterium glutamicum*.

The disclosure also provides a method for constructing the genetic engineering strain according to the above technical solution, including the following steps:

mutating the codon encoding the lysine at position 138 to the codon of cysteine, based on the nucleotide sequence as shown in SEQ ID NO: 4, to obtain a gene having a nucleotide sequence as shown in SEQ ID NO: 3, ligating the gene to an expression vector to obtain a recombinant expression vector, and transforming the recombinant expression vector to a host strain to obtain a genetic engineering strain.

Preferably, the primer for codon mutation of the lysine at position 138 includes an F-primer having a nucleotide sequence as shown in SEQ ID NO: 5 and an R-primer having a nucleotide sequence as shown in SEQ ID NO: 6.

The disclosure also provides the use of the mutant according to the above technical solution or the gene according to the above technical solution or the recombinant expression vector according to the above technical solution or the genetic engineering strain according to the above technical solution or the genetic engineering strain obtained by the construction method according to the above technical solution in fields of food, health products or cosmetics.

Preferably, the use includes increasing the synthesis yield of 2-O-α-D-glycerol glucoside, oligosaccharide, α-arbutin or caffeic acid glucoside.

The invention provides a sucrose phosphorylase mutant with improved enzyme activity. The mutant of the disclosure is based on sucrose phosphorylase derived from *Leuconostoc mesenteroides*, and subjected to site-directed mutagenesis to improve the enzyme activity of sucrose phosphorylase. The improvement of the enzyme activity is conducive to expanding the prospect of industrial application of sucrose phosphorylase for the production of 2-O-α-D-glycerol glucoside and realizing its large-scale industrial application. The test results show that the specific enzyme activity of a pure enzyme solution of the mutant enzyme according to the disclosure, which is obtained from a natural sucrose phosphorylase through modifications of the molecular structure of the sucrose phosphorylase by site-directed mutation biotechnology, is 58% higher than the enzyme activity of the enzyme before mutation, produces 280 g/L of 2-O-α-D-glycerol glucoside by whole-cell transformation, and has a substrate conversion rate of 91%. Moreover, the disclosure shows that the amino acid residue at position 138 has a great influence on the catalytic effect of the enzyme, which provides a certain basis for the study of the catalytic mechanism of the enzyme and improves the industrial application potential of the enzyme.

BRIEF DESCRIPTION OF THE DRAWINGS

FIG. 1 is a diagram showing the conditions of the substrate sucrose and the product converted by recombinant strain C.g ATCC 13032/pXMJ-19-K138C provided by the disclosure at a substrate concentration of 420 g/L, pH 7.0, and a temperature of 35° C. for 20 hours.

DESCRIPTION OF THE EMBODIMENTS

The disclosure provides a sucrose phosphorylase mutant with improved enzyme activity, and the amino acid sequence of the mutant is as shown in SEQ ID NO: 1. The mutant according to the disclosure is obtained by mutating the lysine at position 138 into cysteine based on the amino acid sequence as shown in SEQ ID NO: 2.

The disclosure also provides a gene encoding the mutant according to the above technical solution, and the nucleotide sequence of the gene is as shown in SEQ ID NO: 3.

The disclosure also provides a recombinant expression vector containing the gene described in the above technical solution. In the disclosure, the expression vector preferably comprises a pXMJ-19 plasmid.

The disclosure also provides a genetic engineering strain expressing the sucrose phosphorylase mutant according to the above technical solution. In the disclosure, the host strain of the genetic engineering strain includes *Corynebacterium glutamicum*.

The disclosure also provides a method for constructing the genetic engineering strain according to the above technical solution, including the following steps:

mutating the codon encoding the lysine at position 138 to the codon of cysteine, based on the nucleotide sequence as shown in SEQ ID NO: 4, to obtain a gene having a nucleotide sequence as shown in SEQ ID NO: 3, ligating the gene to an expression vector to obtain a recombinant expression vector, and transforming the recombinant expression vector to a host strain to obtain a genetic engineering strain. In the disclosure, when the expression vector uses the pXMJ-19 plasmid, the obtained recombinant expression vector is named pXMJ-19-K138C, and when the host strain is *C. glutamicum* competent cell ATCC 13032, the obtained genetic engineering strain is named C.g ATCC 13032/pXMJ-19-K138C. In the disclosure, the primer for codon mutation of the lysine at position 138 includes a F-primer having a nucleotide sequence as shown in SEQ ID NO: 5 and a R-primer as shown in SEQ ID NO: 6.

The disclosure also provides the use of the mutant according to the above technical solution or the gene according to the above technical solution or the recombinant expression vector according to the above technical solution or the genetic engineering strain according to the above technical solution or the genetic engineering strain obtained by the construction method according to the above technical solution in the fields of food, health products or cosmetics.

Preferably, the use includes increasing the synthesis yield of 2-O-α-D-glycerol glucoside, oligosaccharide, α-arbutin or caffeic acid glucoside. In the disclosure, the use in the food products also includes the field of food additives. The mutant according to the disclosure can be used for the preparation of cosmetics with whitening effects and food additives that change food flavor. In the disclosure, the use preferably includes increasing the synthesis yield of 2-O-α-D-glycerol glucoside, oligosaccharide, α-arbutin or caffeic acid glucoside.

The sucrose phosphorylase mutant with improved enzyme activity, construction method and use thereof are further described hereinbelow in detail with reference to specific examples. The technical solutions of the disclosure include, but are not limited to, the following examples.

The *Corynebacterium glutamicum* ATCC 13032 involved in the following examples was purchased from BeNa Culture Collection; the pXMJ-19 plasmid involved in the following examples was purchased from PuRuTing Biotechnology (Beijing) Co., Ltd.; the sucrose and glycerol involved in the following examples were purchased from Sinopharm Chemical Reagent Co., Ltd.

The culture media involved in the following examples are as follows:

LB liquid culture medium: peptone 10 g/L, yeast extract 5 g/L, NaCl 10 g/L.

LB solid culture medium (LB plate): peptone 10 g/L, yeast extract 5 g/L, NaCl 10 g/L, 2% agar powder (v/v).

BHI culture medium (g/L): peptone 10, dehydrated calf brain infusion powder 12.5, dehydrated bovine heart infusion powder 5, sodium chloride 5, glucose 2, disodium hydrogen phosphate 2.5, pH 7.2.

The test methods involved in the following examples are as follows:

Enzyme activity is defined as follows: the amount of enzyme required to generate 1 μmol of 2-O-α-D-glycerol glucoside every 1 minute is 1 enzyme activity unit U;

Determination of Enzyme Activity of Sucrose Phosphorylase.

A crude enzyme solution is filtered through a 0.2 μm filter membrane, then subjected to a Ni-NTA affinity chromatography, and eluted with imidazole to obtain a purified enzyme; the reaction system contains 200 mmol/L of sucrose, 400 mmol/L of glycerol, 50 mmol/L of a MES buffer solution of pH 7.0, 100 μL of a pure enzyme solution, which is reacted in a 35° C. water bath for 20 minutes, and reacted in a boiling water bath for 10 minutes to terminate the reaction; the enzyme activity is determined by HPLC method.

HPLC Method: a HPLC differential method is used to determine the substrate and product concentrations; wherein the chromatographic conditions are: chromatographic column: Aminex HPX-87C (300×7.8 mm); mobile phase: ultra-pure water; detector: RID Detector, column temperature: 80° C., injection volume: 10 μL, flow rate: 0.6 mL/min.

Example 1

Construction of a Recombinant Vector Containing the Sucrose Phosphorylase Mutant.

Specific steps were as follows:
(1) Obtaining of a K138C mutant: PCR was performed using the nucleotide sequence as shown in SEQ ID NO: 4 as a template and using a F-primer 1 (the sequence is as shown in SEQ ID NO: 5) and a R-primer 1 (the sequence is as shown in SEQ ID NO: 6) as primers to obtain a recombinant gene as shown in SEQ ID NO: 3.
(2) Double digestion of the recombinant gene and pXMJ-19 with BamH I and EcoI I, respectively, after purification, followed by ligation with a T4DNA ligase overnight at 16° C. Sequencing was performed by Shanghai Sangon Biotech.

Example 2

Construction of a Recombinant Genetic Engineering Strain of *Corynebacterium glutamicum* for Producing the Sucrose Phosphorylase Mutant.

The recombinant plasmid pXMJ-19-K138C obtained in Example 1 was chemically transformed to *E. coli* competent cells. The specific method was as follows:

The solution required for the conversion experiment is as follows (g/L):

LB medium: yeast extract 5, peptone 10, NaCl 10.

50% glycerol, 0.1M CaCl, 115° C. moist heat sterilization.

(1) *E. coli* JM109 or *E. coli* BL21 (DE3) was inoculated in 50 mL of fresh LB broth at 37° C., and grown overnight at 220 r/min.

(2) 1 mL of the overnight culture was inoculated into 100 mL of fresh LB medium at 37° C., and grown with shaking at 220 r/min.

(3) After 1 hour of culture, the $OD_{600}$ value of the culture solution was measured with a spectrophotometer, and it was measured about every 20 minutes until the $OD_{600}$ value reached 0.6 (which required about 2 hours).

(4) The culture solution was divided into 35 mL aliquots, individually subjected to 50 mL centrifugal tubes, and pre-cooled on ice for about 10 minutes.

(5) 1000 g was centrifuged at 4° C. for 5 minutes, and the supernatant was completely discarded.

(6) 2 mL of pre-cooled 0.1M calcium chloride solution was added to a 50 mL centrifugal tube, evenly mixed by slowly pipetting up and down, left to stand still on ice for 15 minutes, and the operation was repeated twice.

(7) Then 3.2 mL of 0.1M calcium chloride solution and 1.6 mL of 50% glycerol were added and dispensed into 1.5 mL centrifugal tubes containing 120 µL each.

*E. coli* competent chemical transformation method: 5 µL of recombinant plasmids were added to 120 µL of competent cells, evenly mixed and placed on ice for half an hour, then subjected to accurate heat shock at 42° C. for 90 seconds, left on ice for 5 minutes, and then added to 800 µL of LB medium, which was incubated at 37° C., 200 r/min, for 90 minutes; the bacterial solution was used to coat a chloramphenicol-resistant plate. Cultivation was performed at 37° C. for 12 hours, and positive transformants were sorted out for test. The recombinant strain *E. coli* BL21/pXMJ-19-K138C, was obtained.

Subsequently, the recombinant strain *E. coli* BL21/pXMJ-19-K138C was inoculated, and after cultivation, the recombinant plasmid pXMJ-19-K138C was extracted, and subjected to electric shock for 5 milliseconds at 1800V using an electroporator; the extracted recombinant plasmid pXMJ-19-K138C was used to electro-transform *Corynebacterium glutamicum* ATCC 13032 competent cells, which were then added to the BHI medium and cultured; the bacterial solution was used to coat a chloramphenicol-resistant plate, which was cultured at 30° C. for 18 hours, and positive transformants were sorted out for test. Finally, the recombinant strain C.g ATCC 13032/pXMJ-19-K138C was obtained.

Example 3

Efficient Expression of Sucrose Phosphorylase from the Recombinant Strain C.g ATCC 13032/pXMJ-19-K138C and Enzyme Activity Determination.

The recombinant strain C.g ATCC 13032/pXMJ-19-K138C constructed in Example 2 and the original strain C.g ATCC 13032/pXMJ-19-SP expressing the non-mutated enzyme were respectively inoculated into 10 mL of chloramphenicol-containing BHI medium, and grown with shaking at 30° C. for 16-20 hours; the next day, 1% of inoculum was transferred to a culture medium for induced expression, and grown at 30° C. for 14 hours; the culture solution was centrifuged at 4° C., 10000 r/min, for 10 minutes; the cell disruption supernatant was an intracellular crude enzyme solution, which was subsequently purified by a Ni column to obtain a pure enzyme solution for the determination of enzyme activity. The enzymatic properties of the pure enzyme were investigated, and the optimal reaction temperature of the sucrose phosphorylase mutant strain was 35° C., and the optimal reaction pH was 7.0.

The results showed that the specific enzyme activity of the sucrose phosphorylase expressed by the recombinant strain C.g ATCC 13032/pXMJ-19-K138C was 10.83 U/mg, and the specific enzyme activity of the original strain C.g ATCC 13032/pXMJ-19-SP as a control was 6.85 U/mg; the specific enzyme activity of the mutated strain was 58% higher than that of the original strain.

The C.g ATCC 13032/pXMJ-19-K138C bacterium bodies obtained by induction were subjected to whole cell transformation to produce 2-O-α-D-glycerol glucoside. In a 1 L transformation system, the bacterium bodies were suspended in MES buffer; the $OD_{600}$ of the bacterium bodies was 50; the pH of the reaction was controlled to be 7.0; at a temperature of 35° C., the rotation speed of the fermentation tank was 200 rpm; 420 g of substrate sucrose, 300 g of glycerol, 1 mL of Triton were added, and 20 hours of conversion could produce 280 g/L of 2-O-α-D-glycerol glucoside with a conversion rate of 91% (The results are shown in FIG. 1, which illustrates the conditions of the substrate sucrose and the product converted by recombinant strain C.g ATCC 13032/pXMJ-19-K138C at a substrate concentration of 420 g/L, pH 7.0, and a temperature of 35° C. for 20 hours; eventually 280 g/L of 2-O-α-D-glycerol glucoside was produced, and the conversion rate was 91%). Under the same conditions, the conversion rate was increased by nearly 26% compared with the conversion rate of the whole cell transformation of the wild-type strain C.g ATCC 13032/pXMJ-19-SP.

The above examples are only preferred embodiments of the disclosure. It should be noted that for those of ordinary skill in the art, without departing from the principles of the disclosure, various improvements and modifications can be made, and these improvements and modifications should be considered to be within the protection scope of the disclosure.

What is claimed:

1. A sucrose phosphorylase mutant, wherein the amino acid sequence of the mutant is as shown in SEQ ID NO: 1.

2. A gene encoding the mutant according to claim 1, wherein the nucleotide sequence of the gene is as shown in SEQ ID NO: 3.

3. A recombinant expression vector containing the gene according to claim 2.

4. A genetic engineering strain expressing the sucrose phosphorylase mutant according to claim 1.

5. The genetic engineering strain according to claim 4, wherein the host strain of the genetic engineering strain includes *Corynebacterium glutamicum*.

6. A food product, a health product or a cosmetic comprising the genetic engineering strain of claim 4 as an ingredient.

7. A method for synthesis of 2-O-α-D-glycerol glucoside comprising contacting the genetic engineering strain of claim 4 with a composition comprising sucrose and glycerol to produce 2-O-α-D-glycerol glucoside.

8. The method of claim 7 wherein the genetic engineering strain comprises a recombinant expression vector containing a gene encoding the amino acid sequence as shown in SEQ ID NO: 1.

9. The method of claim 7 wherein the genetic engineering strain comprises a recombinant expression vector containing a gene having the nucleotide sequence as shown in SEQ ID NO: 3.

10. A method for manufacturing a food product, a health product or a cosmetic comprising contacting the genetic engineering strain of claim 4 with a composition comprising sucrose and glycerol to produce 2-O-α-D-glycerol glucoside, and formulating the 2-O-α-D-glycerol glucoside as an ingredient of the food product, the health product or the cosmetic.

11. A method for constructing the genetic engineering strain according to claim 4, comprising:
   mutating the codon encoding the lysine at position 138 to a codon of cysteine, based on the nucleotide sequence as shown in SEQ ID NO: 4, to obtain a gene having a nucleotide sequence as shown in SEQ ID NO: 3,
   ligating the gene to an expression vector to obtain a recombinant expression vector, and
   transforming the recombinant expression vector to a host strain to obtain a genetic engineering strain.

12. The method of construction according to claim 11, wherein the mutation from the codon of lysine at position 138 to the codon of cysteine is performed by a primer, the primer includes an F-primer having the nucleotide sequence as shown in SEQ ID NO: 5 and an R-primer having the nucleotide sequence as shown in SEQ ID NO: 6.

13. A food product, a health product or a cosmetic comprising the sucrose phosphorylase mutant of claim 1 as an ingredient.

14. A method for manufacturing a food product, a health product or a cosmetic comprising contacting the sucrose phosphorylase mutant of claim 1 with a composition comprising sucrose and glycerol to produce 2-O-α-D-glycerol glucoside, and formulating the 2-O-α-D-glycerol glucoside as an ingredient of the food product, the health product or the cosmetic.

15. A method for synthesis of 2-O-α-D-glycerol glucoside comprising contacting the sucrose phosphorylase mutant of claim 1 with a composition comprising sucrose and glycerol to produce 2-O-α-D-glycerol glucoside.

* * * * *

SEQUENCE LISTING

<160> NUMBER OF SEQ ID NOS: 6

<210> SEQ ID NO 1

```
<211> LENGTH: 492
<212> TYPE: PRT
<213> ORGANISM: artificial sequence
<220> FEATURE:
<223> OTHER INFORMATION: the amino acid sequence of the mutant

<400> SEQUENCE: 1
```

Met Glu Ile Gln Asn Lys Ala Met Leu Ile Thr Tyr Ala Asp Ser Leu
1               5                   10                  15

Gly Lys Asn Leu Lys Asp Val Arg Lys Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ser Asp Tyr Thr Arg Val Asp Ser Ala Phe
    50                  55                  60

Gly Asp Trp Ser Asp Val Glu Ala Leu Gly Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Glu Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Cys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Asp Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Val Leu Thr Asp Glu Glu Ile Asp Tyr Ala Ser Glu Glu Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Ile Phe Gln Val Phe Ala Pro
        355                 360                 365

Gly Ile Pro Gln Ile Tyr Tyr Val Gly Leu Leu Ala Gly Glu Asn Asp
    370                 375                 380

```
Ile Glu Leu Leu Glu Ser Ser Lys Glu Gly Arg Asn Ile Asn Arg His
385                 390                 395                 400

Tyr Tyr Ser Val Asp Glu Val Lys Glu Val Lys Arg Pro Val Val
            405                 410                 415

Ala Lys Leu Leu Lys Leu Leu Ser Trp Arg Asn Asn Phe Ala Ala Phe
        420                 425                 430

Asp Leu Asp Gly Ser Ile Asp Val Glu Thr Pro Ser Asp Thr Thr Ile
        435                 440                 445

Lys Ile Thr Arg Lys Asp Lys Ser Gly Glu Asn Val Ala Val Leu Val
        450                 455                 460

Ala Asn Ala Ala Asp Lys Thr Phe Thr Ile Thr Ala Asn Gly Glu Glu
465                 470                 475                 480

Ile Leu Ala Asn Thr Glu Ala Asp Lys Gln Gln Leu
                485                 490
```

<210> SEQ ID NO 2
<211> LENGTH: 492
<212> TYPE: PRT
<213> ORGANISM: artificial sequence
<220> FEATURE:
<223> OTHER INFORMATION: the amino acid sequence before mutation

<400> SEQUENCE: 2

```
Met Glu Ile Gln Asn Lys Ala Met Leu Ile Thr Tyr Ala Asp Ser Leu
1               5                   10                  15

Gly Lys Asn Leu Lys Asp Val Arg Lys Val Leu Lys Glu Asp Ile Gly
                20                  25                  30

Asp Ala Ile Gly Gly Val His Leu Leu Pro Phe Phe Pro Ser Thr Gly
            35                  40                  45

Asp Arg Gly Phe Ala Pro Ser Tyr Thr Arg Val Asp Ser Ala Phe
        50                  55                  60

Gly Asp Trp Ser Asp Val Glu Ala Leu Gly Glu Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Glu Ser Lys Tyr Lys Asp Phe Phe Ile
                100                 105                 110

Arg Trp Glu Lys Phe Trp Ala Lys Ala Gly Glu Asn Arg Pro Thr Gln
            115                 120                 125

Ala Asp Val Asp Leu Ile Tyr Lys Arg Lys Asp Lys Ala Pro Thr Gln
        130                 135                 140

Glu Ile Thr Phe Asp Asp Gly Thr Thr Glu Asn Leu Trp Asn Thr Phe
145                 150                 155                 160

Gly Asp Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
        210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255
```

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Val Leu Thr Asp Glu Glu Ile Asp Tyr Ala Ser Glu Glu Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350

Asp Asp Ala Ala Tyr Leu Leu Ser Arg Ile Phe Gln Val Phe Ala Pro
        355                 360                 365

Gly Ile Pro Gln Ile Tyr Tyr Val Gly Leu Leu Ala Gly Glu Asn Asp
    370                 375                 380

Ile Glu Leu Leu Glu Ser Ser Lys Glu Gly Arg Asn Ile Asn Arg His
385                 390                 395                 400

Tyr Tyr Ser Val Asp Glu Val Lys Glu Val Lys Arg Pro Val Val
                405                 410                 415

Ala Lys Leu Leu Lys Leu Leu Ser Trp Arg Asn Asn Phe Ala Ala Phe
            420                 425                 430

Asp Leu Asp Gly Ser Ile Asp Val Glu Thr Pro Ser Asp Thr Thr Ile
        435                 440                 445

Lys Ile Thr Arg Lys Asp Lys Ser Gly Glu Asn Val Ala Val Leu Val
    450                 455                 460

Ala Asn Ala Ala Asp Lys Thr Phe Thr Ile Thr Ala Asn Gly Glu Glu
465                 470                 475                 480

Ile Leu Ala Asn Thr Glu Ala Asp Lys Gln Gln Leu
            485                 490

<210> SEQ ID NO 3
<211> LENGTH: 1479
<212> TYPE: DNA
<213> ORGANISM: artificial sequence
<220> FEATURE:
<223> OTHER INFORMATION: the nucleotide sequence of the gene encoding
      the mutant

<400> SEQUENCE: 3
atggaaattc aaaataaagc aatgctcatc acatacgctg attcattggg taaaaacttg      60
aaggatgttc gcaaagtctt gaaagaagat attggtgatg caattggtgg tgttcacttg     120
ttgccatttt tcccatcaac gggagaccgc ggttttgcac cttctgatta cacacgtgtt     180
gattcagcat ttggtgattg gagtgatgta gaagcattag gtgaagaata ttacttgatg     240
tttgatttca tgattaacca tatttcacgt gaatctgtta tgtatcaaga tttcaagaag     300
aatcatgatg aatcaaaata taggatttc ttcattcgct gggaaaagtt ctgggccaag     360
gctggtgaaa accgtccaac acaagccgat gttgacttga tttacaagcg taaggattgt     420
gcaccaactc aagaaattac ttttgatgat ggtacaactg aaaacttgtg aacacatttt     480
ggtgatgaac aaattgatat cgatgtaaac tcagctatcg ctaaagaatt tatcaagaca     540
acgcttgaag catggtgaa gcatggagct aacttgattc gtttggatgc ctttgcatac     600
gctgttaaaa aagttgatac aaatgacttc ttcgttgaac ctgaaatctg ggatacattg     660

```
aacgaggttc gtgaaatttt gacacctttg aaggccgaaa ttttgccaga aatccatgaa      720
cactattcaa ttcctaagaa gatcaatgat catggttact tcacatatga ttttgctttg      780
ccaatgacga cactttatac attgtattca ggtaaaacaa atcaattggc taaatggttg      840
aagatgtcac caatgaagca atttactact ttggatacgc acgacggtat aggtgttgtt      900
gatgcgcgtg acgtcttgac tgatgaagaa attgattatg catctgaaga gttatacaaa      960
gttggtgcta acgtgaagaa gacttactct tctgcttcat acaacaactt ggatatctac     1020
caaatcaact caacatatta ctcagctttg ggaaatgatg atgctgcgta cttgctaagc     1080
cgtatcttcc aagtgttcgc tcctggtatt ccacaaatct actatgttgg tttgttggcc     1140
ggtgaaaatg atattgaatt acttgaatct tcaaaagaag gtcgtaacat caaccgtcat     1200
tactactcag ttgatgaagt taaggaagaa gttaagcgcc cagttgttgc taagttgttg     1260
aagcttttgt catggcgtaa caactttgct gcatttgatt tggacggatc aattgacgtt     1320
gaaacaccat ctgatacaac tatcaagatt actcgtaagg ataagtctgg tgaaaatgtt     1380
gcagtcttgg ttgccaacgc tgccgataag acattcacaa tcactgcaaa tggtgaagaa     1440
atcttagcca acacagaagc tgataagcaa caattgtaa                            1479
```

<210> SEQ ID NO 4
<211> LENGTH: 1478
<212> TYPE: DNA
<213> ORGANISM: artificial sequence
<220> FEATURE:
<223> OTHER INFORMATION: the nucleotide sequence of the gene before
      mutation

<400> SEQUENCE: 4

```
atggaaattc aaaataaagc aatgctcatc acatacgctg attcattggg taaaaacttg       60
aaggatgttc gcaaagtctt gaaagaagat attggtgatg caattggtgg tgttcacttg      120
ttgccatttt tcccatcaac gggagaccgc ggttttgcac cttctgatta cacacgtgtt      180
gattcagcat ttggtgattg gagtgatgta gaagcattag gtgaagaata ttacttgatg      240
tttgatttca tgattaacca tatttcacgt gaatctgtta tgtatcaaga tttcaagaag      300
aatcatgatg aatcaaaata taaggatttc ttcattcgct gggaaaagtt ctgggccaag      360
gctggtgaaa accgtccaac acaagccgat gttgacttga tttacaagcg taaggataag      420
gcaccaactc aagaaattac ttttgatgat ggtacaactg aaaacttgtg gaacacatt t     480 ggtgatgaac aaattgatat cgatgtaaac tcagctatcg ctaaagaatt tatcaagaca      540
acgcttgaag acatggtgaa gcatggagct aacttgattc gtttggatgc ctttgcatac      600
gctgttaaaa agttgatac aaatgacttc ttcgttgaac ctgaaatctg ggatacattg      660
aacgaggttc gtgaaatttt gacacctttg aaggccgaaa ttttgccaga aatccatgaa      720
cactattcaa ttcctaagaa gatcaatgat catggttact tcacatatga ttttgctttg      780
ccaatgacga cactttatac attgtattca ggtaaaacaa atcaattggc taaatggttg      840
aagatgtcac caatgaagca atttactact ttggatacgc acgacggtat aggtgttgtt      900
gatgcgcgtg acgtcttgac tgatgaagaa attgattatg catctgaaga gttatacaaa      960
gttggtgcta acgtgaagaa gacttactct tctgcttcat acaacaactt ggatatctac     1020
caaatcaact caacatatta ctcagctttg ggaaatgatg atgctgcgta cttgctaagc     1080
cgtatcttcc aagtgttcgc tcctggtatt ccacaaatct actatgttgg tttgttggcc     1140
ggtgaaaatg atattgaatt acttgaatct tcaaaagaag gtcgtaacat caaccgtcat     1200
```

```
actactcagt tgatgaagtt aaggaagaag ttaagcgccc agttgttgct aagttgttga      1260
agcttttgtc atggcgtaac aactttgctg catttgattt ggacggatca attgacgttg      1320
aaacaccatc tgatacaact atcaagatta ctcgtaagga taagtctggt gaaaatgttg      1380
cagtcttggt tgccaacgct gccgataaga cattcacaat cactgcaaat ggtgaagaaa      1440
tcttagccaa cacagaagct gataagcaac aattgtaa                             1478
```

<210> SEQ ID NO 5
<211> LENGTH: 37
<212> TYPE: DNA
<213> ORGANISM: artificial sequence
<220> FEATURE:
<223> OTHER INFORMATION: F-primer

<400> SEQUENCE: 5

```
atttacaagc gttgtgataa ggcaccaact caagaaa                              37
```

<210> SEQ ID NO 6
<211> LENGTH: 35
<212> TYPE: DNA
<213> ORGANISM: artificial sequence
<220> FEATURE:
<223> OTHER INFORMATION: R-primer

<400> SEQUENCE: 6

```
tggtgcctta tcacaacgct tgtaaatcaa gtcaa                                35
```